(12) United States Patent
Fayram et al.

(10) Patent No.: US 8,147,416 B2
(45) Date of Patent: Apr. 3, 2012

(54) IMPLANTABLE SYSTEMIC BLOOD PRESSURE MEASUREMENT SYSTEMS AND METHODS

(75) Inventors: Timothy A. Fayram, Gilroy, CA (US); Eric S. Fain, Sunnyvale, CA (US); Paul A. Levine, Santa Clarita, CA (US); Anders Björling, Solna (SE)

(73) Assignee: Pacesetter, Inc., Sunnyvale, CA (US)

( * ) Notice: Subject to any disclaimer, the term of this patent is extended or adjusted under 35 U.S.C. 154(b) by 1249 days.

(21) Appl. No.: 11/848,586

(22) Filed: Aug. 31, 2007

(65) Prior Publication Data
US 2009/0062667 A1    Mar. 5, 2009

(51) Int. Cl.
*A61B 5/02* (2006.01)
*A61B 5/021* (2006.01)

(52) U.S. Cl. ......... 600/486; 600/485; 600/481; 600/504

(58) Field of Classification Search ........... 600/481–507
See application file for complete search history.

(56) References Cited

U.S. PATENT DOCUMENTS

| | | | |
|---|---|---|---|
| 4,425,920 A | 1/1984 | Bourland et al. |
| 4,676,253 A | 6/1987 | Newman |
| 4,791,931 A | 12/1988 | Slate |
| 5,857,975 A | 1/1999 | Golub |
| 5,862,805 A | 1/1999 | Nitzan |
| 5,865,755 A | 2/1999 | Golub |
| 6,120,459 A | 9/2000 | Nitzan et al. |
| 6,122,536 A | 9/2000 | Sun |
| 6,575,912 B1 | 6/2003 | Turcott |
| 6,599,251 B2 | 7/2003 | Chen |
| 6,647,287 B1 | 11/2003 | Peel |
| 6,648,828 B2 | 11/2003 | Friedman et al. |
| 6,731,967 B1 | 5/2004 | Turcott |
| 6,942,622 B1 | 9/2005 | Turcott |
| 6,997,879 B1 | 2/2006 | Turcott |
| 7,029,447 B2 | 4/2006 | Rantala |
| 7,125,383 B2 | 10/2006 | Hoctor |
| 7,212,861 B1 | 5/2007 | Park |
| 7,286,875 B1 | 10/2007 | Park |

(Continued)

FOREIGN PATENT DOCUMENTS
EP    0256159 B1    5/1991
(Continued)

OTHER PUBLICATIONS

25, *Impedance Plethysmography*—http://www.bem.fi/book/25/25.htm.

(Continued)

*Primary Examiner* — Miranda Le
*Assistant Examiner* — Eric Messersmith
(74) *Attorney, Agent, or Firm* — Steven M. Mitchell

(57) ABSTRACT

Implantable systems, and methods for use therewith, for monitoring arterial blood pressure on a chronic basis are provided herein. A first signal indicative of electrical activity of a patient's heart, and a second signal indicative of mechanical activity of the patient's heart, are obtained using implanted electrodes and an implanted sensor. By measuring the times between various features of the first signal relative to features of the second signal, values indicative of systolic pressure and diastolic pressure can be determined. In specific embodiments, such features are used to determine a peak pulse arrival time (PPAT), which is used to determine the value indicative of systolic pressure. Additionally, a peak-to-peak amplitude at the maximum peak of the second signal, and the value indicative of systolic pressure, can be used to determine the value indicative of diastolic pressure.

26 Claims, 6 Drawing Sheets

U.S. PATENT DOCUMENTS

| | | | |
|---|---|---|---|
| 2004/0030261 A1* | 2/2004 | Rantala | 600/561 |
| 2004/0167417 A1* | 8/2004 | Schulhauser et al. | 600/513 |
| 2004/0171945 A1* | 9/2004 | Narimatsu | 600/490 |
| 2005/0131306 A9 | 6/2005 | Mills | |
| 2005/0251059 A1 | 11/2005 | Kim | |
| 2005/0261593 A1 | 11/2005 | Zhang | |
| 2006/0074322 A1 | 4/2006 | Nitzan | |
| 2007/0276632 A1 | 11/2007 | Banet et al. | |
| 2008/0033305 A1 | 2/2008 | Hatib et al. | |
| 2008/0039731 A1 | 2/2008 | McCombie | |
| 2008/0183083 A1 | 7/2008 | Markowitz et al. | |
| 2008/0183232 A1 | 7/2008 | Voss | |

FOREIGN PATENT DOCUMENTS

| | | |
|---|---|---|
| EP | 0443267 A1 | 8/1991 |
| EP | 0307093 B1 | 12/1995 |

OTHER PUBLICATIONS

Stewart et al., "Pseudo-QT Prolongation, Artifactual Electrocardiographic Patterns Produced by Transduction of Cardiovascular Motion," Pacing Clin. Electrophysiol., vol. 6 (Part 1), pp. 940-947 (Sep. 1983).

Allen, "Photoplethysmography and its Application in Clinical Physiological Measurement," Physiol. Meas. 28 (2007) R1-R39.

Chen et al., "Continuous Estimation of Systolic Blood Pressure Using the Pulse Arrival Time and Intermittent Calibration," Medical & Bilogical Engineering & Computing 2000, vol. 38, pp. 569-574.

Turcott et al., "Subcutaneous Photoplethysmography in Extravascular Hemodynamic Sensing," 47 pages.

Turcott et al., "Atrio-Ventricular Delay Optimization using Subcutaneous Photoplethysmography," 41 pages.

Payne et al., "Pulse Transit Time Measured from the ECG: An Unreliable Marker of Beat-to-Beat Blood Pressure," American Physiological Society, 2006, pp. 136-141.

Poon et al., "Cuff-less and Noninvasive Measurements of Arterial Blood Pressure by Pulse Transit Time," IEEE 2005, Engineering in Medican and Biology 27$^{th}$ Annual Conference, pp. 5877-5880.

Sameshima et al., "Continuous Systolic Blood Pressure Monitoring by the Difference in Electrocardiogram and Pulse Oximetry in Near-Term, Exteriorized Goat Fetuses," Journal of the Society for Gynecologic Investigation 2003; 10; 200; 6 pages.

* cited by examiner

IMPLANTABLE SYSTEMIC BLOOD PRESSURE MEASUREMENT SYSTEMS AND METHODS

FIELD OF THE INVENTION

Embodiments of the present invention relate to implantable systems for monitoring arterial blood pressure, and methods for use therewith.

BACKGROUND OF THE INVENTION

A person's circulatory system includes both systemic and pulmonary circulation systems. Pulmonary circulation supplies the lungs with blood flow, while the systemic circulation takes care of all the other parts of the body, i.e. the systemic circulation. The heart serves as a pump that keeps up the circulation of the blood. Both the pulmonary and systemic circulatory systems are made up of arteries, arterioles, capillaries, venules and veins. The arteries take the blood from the heart, while the veins return the blood to the heart Blood pressure is defined as the force exerted by the blood against any unit area of the vessel wall. The measurement unit of blood pressure is millimeters of mercury (mmHg). Pulmonary and systemic arterial pressures are pulsatile, having systolic and diastolic pressure values. The highest recorded pressure reading is called systolic pressure, which results from the active contraction of the ventricle. Although the arterial pressure and indeed flow in the arteries is pulsatile, the total volume of blood in the circulation remains constant. The lowest pressure reading is called diastolic pressure which is maintained by the resistance created by the smaller blood vessels still on the arterial side of the circulatory system (arterioles). Stated another way, the systolic pressure is defined as the peak pressure in the arteries, which occurs near the beginning of a cardiac cycle. In contrast, the diastolic pressure is the lowest pressure, which occurs at the resting phase of the cardiac cycle. The pulse pressure reflects the difference between the maximum and minimum pressures measured (i.e., the difference between the systolic pressure and diastolic pressure). The mean arterial pressure is the average pressure throughout the cardiac cycle.

Arterial pulse pressure, such as mean arterial pressure (MAP), is a fundamental clinical parameter used in the assessment of hemodynamic status of a patient. Mean arterial pressure can be estimated from real pressure data in a variety of ways. Among the techniques that have been proposed, two are presented below. In these formulas, SP is the systolic blood pressure, and DP is diastolic pressure.

a. $MAP_2 = (SP + 2DP)/3 = \frac{1}{3}(SP) + \frac{2}{3}(DP)$ b. $MAP_1 = (SP + DP)/2$ Systolic pressure and diastolic pressure can be obtained in a number of ways. A common approach is to use a stethoscope, an occlusive cuff, and a pressure manometer. However, such an approach is slow, requires the intervention of a skilled clinician and does not provide timely readings as it is a measurement at only a single point in time. While systolic pressure and diastolic pressure can also be obtained in more automated fashions, it is not always practical to obtain measures of pressure using a cuff and pressure transducer combination, especially if the intention or desire is to implant a sensor that can monitor arterial pressure on a chronic basis.

Another approach for obtaining measures of arterial pressure is to use an intravascular pressure transducer. However, an intravascular device may cause problems, such as, embolization, nerve damage, infection, bleeding and/or vessel wall damage. Additionally, the implantation of an intravascular lead requires a highly skilled physician such as a surgeon, electrophysiologist, or interventional cardiologist.

Plethysmography, the measurement of volume of an organ or body part, has a history that extends over 100 years. Photoplethysmography (PPG) uses optical techniques to perform volume measurements, and was first described in the 1930s. While best known for their role in pulse oximetry, PPG sensors have also been used to indirectly measure blood pressure. For example, non-invasive PPG sensors have been used in combination with in an inflatable cuff in a device known as Finapres. U.S. Pat. Nos. 4,406,289 (Wesseling et al.) and 4,475,940 (Hyndman) are exemplary patents that relate to the Finapres technique. The cuff is applied to a patient's finger, and the PPG sensor measures the absorption at a wavelength specific for hemoglobin. After the cuff is used to measure the individual's mean arterial pressure, the cuff pressure around the finger is then varied to maintain the transmural pressure at zero as determined by the PPG sensor. The Finapres device tracks the intra-arterial pressure wave by adjusting the cuff pressure to maintain the optical absorption constant at all times.

There are a number of disadvantages to the Finapres technique. For example, when there exists peripheral vasoconstriction, poor vascular circulation, or other factors, the blood pressure measured in a finger is not necessarily representative of central blood pressure. Further, maintaining continuous cuff pressure causes restriction of the circulation in the finger being used, which is uncomfortable when maintained for extended periods of time. Accordingly, the Finapres technique is not practical for chronic use. Additionally, because of the need for a pneumatic cuff, a Finapres device can not be used as an implanted sensor.

Simple external blood pressure monitors also exist, but they do not offer continuous measurement and data logging capability. These devices can be purchased at a drug store, but patient compliance is required to make regular measurements and accurately record the data. Additionally, portable external miniature monitors that automatically log blood pressure data exist, but these devices can only store a day or so of data and require clinician interaction to download and process the measured data.

As is evident from the above description, there is the need for improved systems and methods for monitoring arterial blood pressure, including systolic pressure, diastolic pressure and mean arterial pressure.

SUMMARY OF THE INVENTION

Embodiments of the present invention relate to implantable systems, and methods for use therewith, for monitoring a patient's arterial blood pressure. Implanted electrodes are used to obtain a first signal indicative of electrical activity of the patient's heart, such as an intracardiac electrogram (IEGM) as recorded from electrodes placed within the heart or electrocardiogram (ECG) as recorded from electrodes in a subcutaneous location. Additionally, an implanted sensor is used to obtain a second signal indicative of mechanical activity of the patient's heart. For example, an implanted plethysmography sensor can be used to obtain a plethysmography signal. In specific embodiments, the implanted plethysmography sensor is a photoplethysmography (PPG) sensor that obtains a PPG signal.

In accordance with specific embodiments, a ventricular depolarization and a ventricular repolarization is detected in a portion of the first signal corresponding to a cardiac cycle. Ventricular depolarization can be detected by detecting an R-wave in the portion of the first signal corresponding to the cardiac cycle, and ventricular repolarization can be detected by detecting a T-wave in the portion of the first signal corresponding to the cardiac cycle. Additionally, a maximum peak amplitude is detected in a portion of the second signal corresponding to the same cardiac cycle. This enables specific times to be determined, including a time $t_1$ from the detected ventricular depolarization to the detected maximum peak amplitude in the second signal, and a time $t_2$ from the detected ventricular repolarization to the detected maximum peak amplitude in the second signal.

Based on the times $t_1$ and $t_2$, a peak pulse arrival time (PPAT) is determined. For example, the PPAT can be the mean of times $t_1$ and $t_2$, but use of alternative equations are also possible. A value indicative of systolic pressure (SP) can then be determined based on the PPAT.

In alternative embodiments, $t_1$, but not $t_2$, is determined, and a pulse arrival time (PAT) is determined based on $t_1$. In such embodiments, a value indicative of SP is determined based on the PAT.

Additionally, a peak-to-peak amplitude $a_1$ in the second signal can be determined, and a value indicative of diastolic pressure (DP) can be determined based on the amplitude a1 and the value indicative of SP. This can include determining a value indicative of pulse pressure (PP) based on the amplitude $a_1$, and determining a value indicative of diastolic pressure (DP) by subtracting the value indicative of PP from the value indicative of SP. Values of SP and DP can be stored in memory of the implantable system, and data indicative of the stored values indicative of SP and DP can be wireless transmitted to a non-implanted device, e.g., for display to a physician.

In accordance with specific embodiments of the present invention, the above described method is repeated over time to thereby track changes in SP and DP. In specific embodiments, an activity sensor and/or posture sensor can be used to trigger the performance of the above described method.

In certain embodiments, an alarm can be triggered based on comparisons of the values indicative of SP, the values indicative of DP, the changes in SP and/or the changes in DP, to corresponding thresholds. Such an alarm can be part of the implanted system, or a non-implanted alarm can be triggered.

Other features and advantages of the invention will appear from the following description in which the preferred embodiments have been set forth in detail, in conjunction with the accompanying drawings and claims.

DETAILED DESCRIPTION OF THE INVENTION

Figure 1:
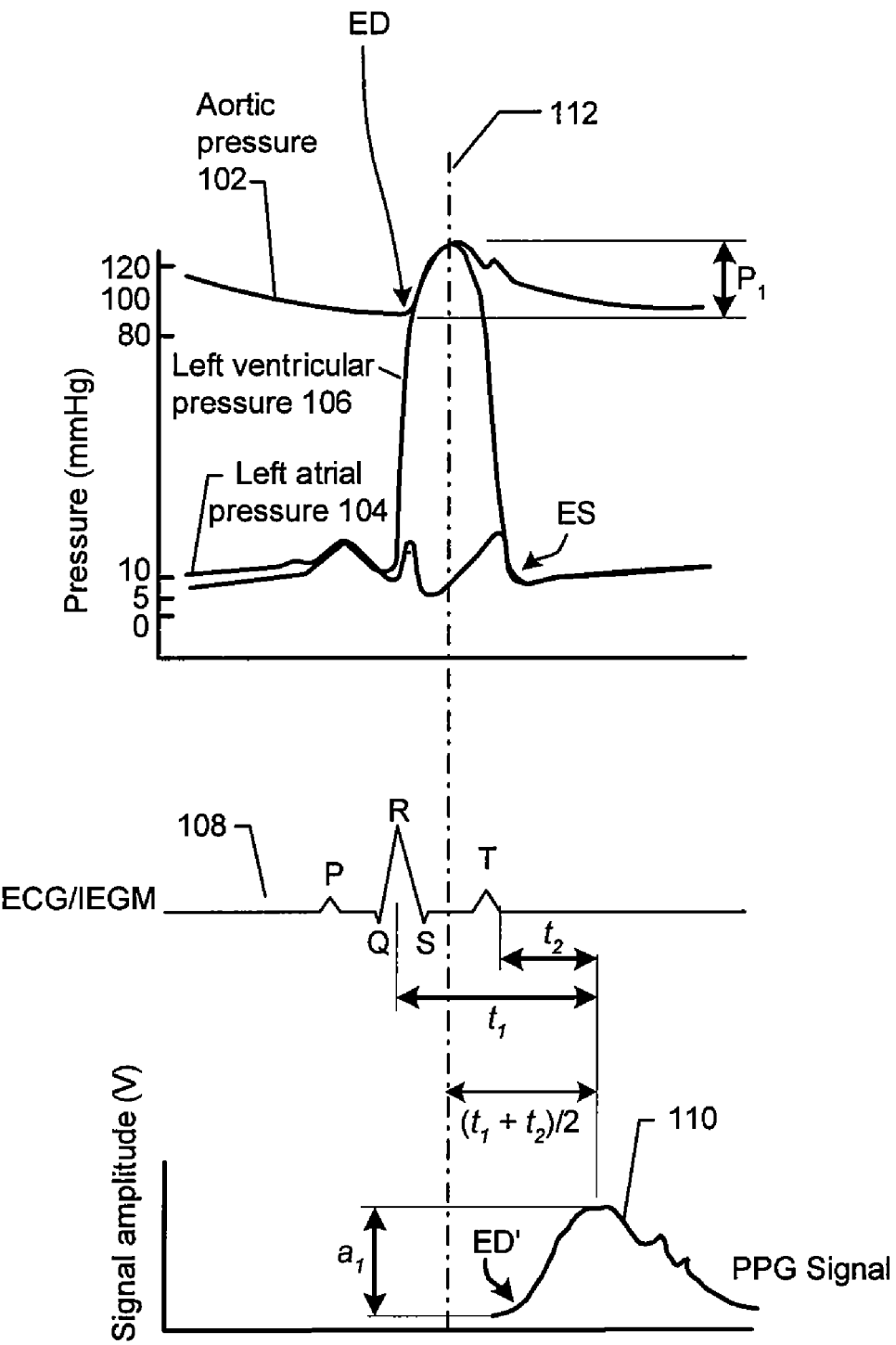
FIG. 1 includes signal waveforms that are used to show the relative timing of electrical and mechanical cardiac events that occur during a cardiac cycle. The upper graph includes an aortic pressure waveform, a left atrial pressure waveform and a left ventricular pressure waveform. The middle graph includes a signal indicative of electrical cardiac activity. The lower graph includes a photoplethysmography (PPG) signal, which is indicative of mechanical cardiac activity.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Referring to FIG. 1, the signal waveforms therein are used to show the relative timing of electrical and mechanical cardiac events that occur during a cardiac cycle. The upper graph includes an aortic pressure waveform 102, a left atrial pressure waveform 104 and a left ventricular pressure waveform 106. The middle graph includes an electrocardiogram (ECG) or intracardiac electrogram (IEGM) waveform 108, which is shown as including a P wave, a QRS complex (including Q, R and S waves) and a T wave. The P wave is caused by depolarization of the atria. This is followed by atrial contraction, which is indicated by a slight rise in the atrial pressure (seen in waveform 104) contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T wave and this is associated with the onset of ventricular relaxation in which forward flow stops, the pressure in the ventricle falls below that in the atria at which time the mitral and tricuspid valves open to begin to passively fill the ventricle during diastole. Also shown in FIG. 1, in the bottom graph, is a photoplethysmography (PPG) signal 110, which will be described in additional detail below.

In accordance with specific embodiments of the present invention, an IEGM signal (e.g., like 108) is obtained using implanted electrodes on endocardial lead(s), which typically provide for better fidelity than an ECG signal obtained from non-implanted surface electrodes. Additionally, a signal indicative of mechanical activity of a patients heart, such as a plethysmography signal (e.g., like 110), is obtained from an implanted sensor. In accordance with specific embodiments of the present invention, by detecting the timing and amplitude of certain features of such signals, various arterial blood pressure measurements can be obtained, including systolic pressure, diastolic pressure, pulse pressure and/or mean arterial pressure. As mentioned above, the systolic pressure (SP) is the peak pressure in the arteries, which occurs near the beginning of a cardiac cycle. The diastolic pressure (DP) is the lowest pressure in the arteries, which occurs at the end of the resting phase of the cardiac cycle. The pulse pressure (PP) is the difference between the systolic and diastolic pressures. The mean arterial pressure (MAP) is a weighted average of pressure throughout the cardiac cycle.

Because implanted electrodes and an implanted sensor are used to obtain the various arterial pressure measurements, a patient's arterial blood pressure can be monitored on a chronic basis. Thus, arterial blood pressure can be tracked to monitor a patient's worsening (or improving) cardiac disease state, and to trigger alerts and/or titration of blood pressure medications. Additionally, arterial blood pressure measurements can be used as a measure of hemodynamic function, and thus used in a closed loop for hemodynamic optimization (e.g., A-V delay, VV delay, and/or pacing rate optimization).

Embodiments of the present invention can be implemented within a pacemaker or ICD system, or as part of an implantable monitor that does not pace and/or shock a patient's heart. Additional details of such embodiments are provided below.

Embodiments of the present invention use the concept of pulse arrival time, also known as pulse transmit time, or pulse wave velocity to monitor arterial blood pressure. However, embodiments of the present invention differ from most prior art systems that rely on pulse arrival time, because most prior art systems are non-implanted. Accordingly, most prior are systems that rely on pulse arrival time are not practical for chronic use.

The inventors of the present invention are aware of one prior art reference, i.e., U.S. Pat. No. 4,425,920 (Bourland et al.), that does suggest an implantable system for monitoring arterial blood pressure using the concept of pulse transmit time. However, the system of the '920 patent requires that two sets of electrodes be positioned adjacent an artery at two sites, and thus, requires very precise and potentially difficult implantation of its system. In contrast, the implantable systems of the present invention can be implanted in the same manner as any conventional pacemaker/ICD is implanted, or potentially in a simpler manner (if the system of the present invention is implemented in a monitor that does not pace and/or shock a patient's heart).

Additionally, many embodiments of the present invention use a novel measure, referred to below as peak pulse arrival time (PPAT), which is believed to provide for improved measures of arterial blood pressure. Referring to FIG. 1, it can be seen that a time of the peak arterial blood pressure, represented by dashed line 112, occurs at a time between ventricular depolarization (as represented by the QRS complex) and ventricular repolarization (as represented by the T wave). More specifically, it can be seen that the peak occurs generally halfway between the QRS complex and the T wave. PPAT is determined, taking this into account.

As can also be seen from FIG. 1, the peak in the PPG signal 110 occurs at a time after the peak in the arterial blood pressure (as shown in the upper graph). This is because the peak in the PPG signal 110 is indicative of the peak wave in arterial blood pressure generated by the patient's heart, as detected by a PPG sensor located a distance from the patient's heart. Presuming the PPG sensor is implanted in the pectoral region of the patient (which is an option, but not necessary), the time that it takes a peak pulse wave (as detected from ECG/IEGM electrodes) to travel from the patient's heart to the PPG sensor can be, e.g., on the order of 10-100 msec, depending on the location of the electrodes (used to obtain the ECG/IEGM) and the location of the PPG sensor. The peak pulse wave is initially detectable from an ECG/IEGM obtained using implanted electrodes. The time at which the peak wave reaches the implanted PPG sensor is detectable from a PPG signal produced by the implanted PPG sensor. Accordingly, in accordance with embodiments of the present invention, the amount of time it takes a peak pulse wave to travel from the patient's heart to the PPG sensor can be determined. Such information is used to determine values of arterial blood pressure. It is also possible, and within the scope of the present invention, that the time it takes a peak pulse to travel from the patient's heart to the PPG sensor can be outside the 10-100 msec range mentioned above.

Figure 2A:
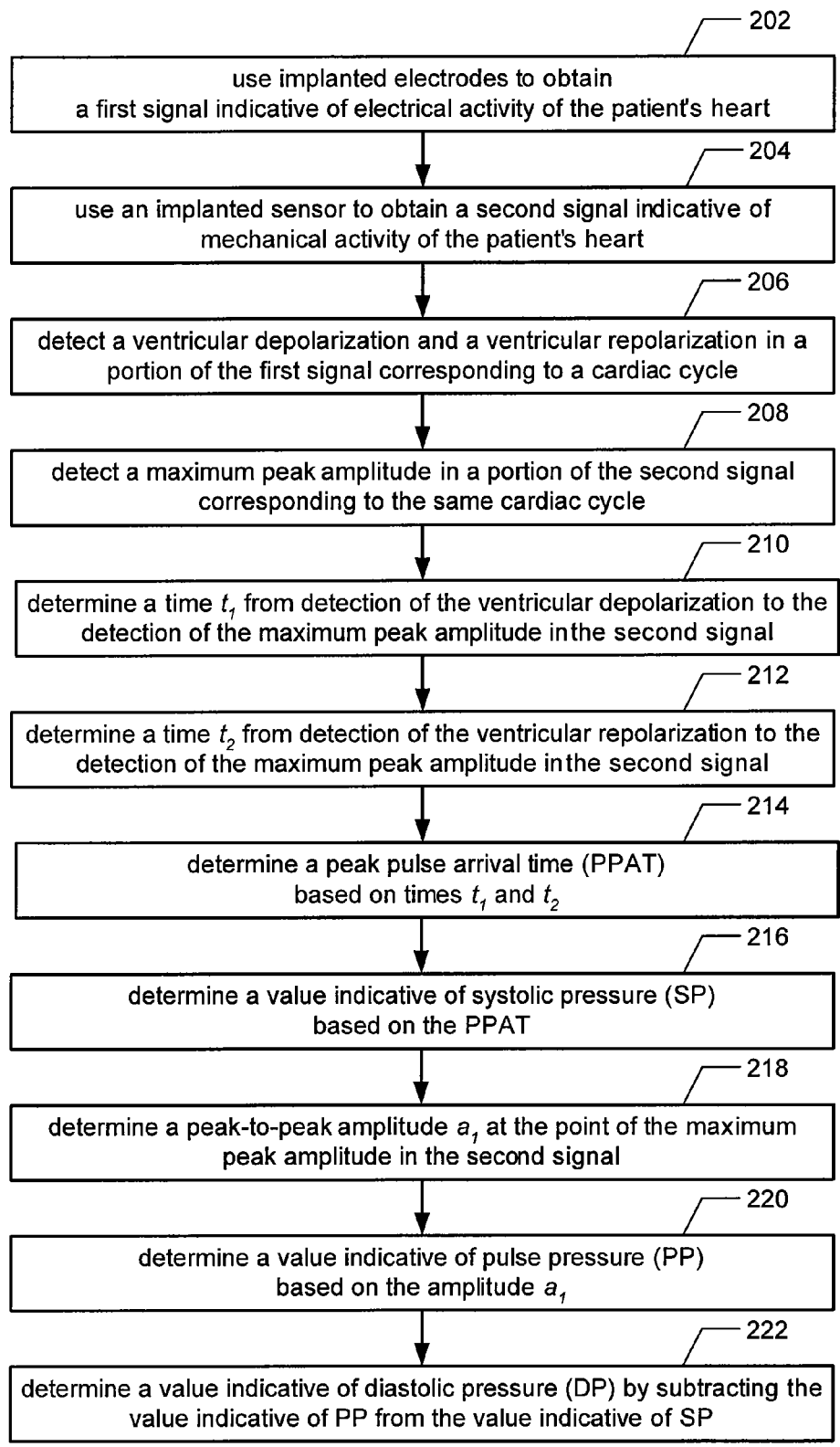
FIG. 2A is a high level flow diagram that is used to explain specific embodiments of the present invention.
Figure 2B:
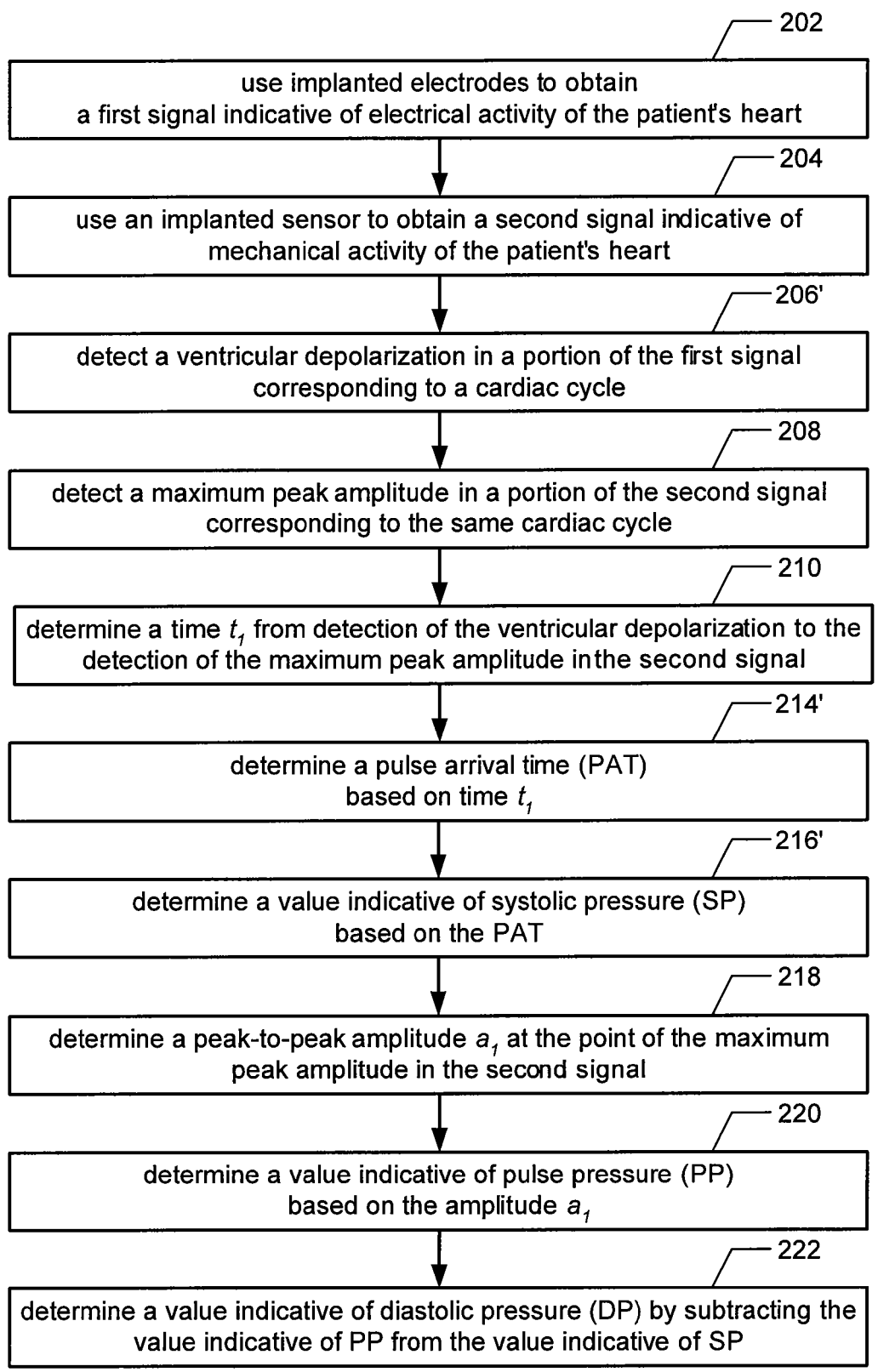
FIG. 2B is a high level flow diagram that is used to explain alternative embodiments of the present invention.

Embodiments of the present invention will first be summarized with reference to the high level flow diagrams of FIGS. 2A and 2B. Following the discussion of the flow diagrams, exemplary implantable systems of the present invention will be described, including discussions of exemplary implantable electrodes and sensors that can be used. In the flow diagrams, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 2A, at step 202, implanted electrodes are used to obtain a first signal indicative of electrical activity of the patient's heart. The first signal can be an intracardiac electrogram (IEGM) obtained using one or more electrode of an endocardial lead, examples of which are discussed below with reference to FIGS. 3A and 4. Alternatively, the first signal can be an electrocardiogram (ECG) obtained using one or more subcutaneous electrode. A portion of an exemplary first signal indicative of electrical activity of the patient's heart is shown at 108 in FIG. 1.

At step 204, an implanted sensor is used to obtain a second signal indicative of mechanical activity of the patient's heart. In specific embodiments, the second signal can is a plethysmography signal, such as, but not limited to, a photoplethysmography (PPG) signal. An exemplary PPG sensor, also referred to as an implanted optical sensor, is discussed below with reference to FIGS. 3A-3C and 4. An exemplary portion of a PPG signal is shown at 110 in FIG. 1. Alternatively, the second signal can be an impedance plethysmography signal. In still other embodiments, the second signal can be a signal output by a sensor including a piezo-electric diaphragm. Alternative sensors that can be used to produce the second signal, include, but are not limited to, a close range microphone, a sensor including a small mass on the end of a piezo bending beam with the mass located on the surface of a small artery, a transmission mode infrared motion sensor sensing across the surface of a small artery, or a MEMS accelerometer located on the surface of a small artery. Such alternative sensors can be located, e.g., on the tip of a short lead connected to a device header that is subcutaneously implanted in closed proximity to an implanted stimulation device. The implanted sensor is preferably extravascular, and preferably a sufficient distance from the patient's heart such that meaningful changes in the amount of time it takes a pulse wave originating in the heart to reach the implanted sensor can be detected, thereby enabling changes in arterial blood pressure to be detected. For example, it is preferred that the implanted sensor (used to obtain the second signal indicative of mechanical activity of the patient's heart) is at least 10 mm from the patient's aortic root. Such a second sensor can be implanted, e.g., in the pectoral region of a patient. Thus, it is practical that the second sensor can be integrated with or attached to the housing of a pacemaker or ICD, as can be appreciated from FIGS. 3A-3C and 4 discussed below. Alternative locations for implantation of the second sensor include, but are not limited to, the patient's leg, arm or neck.

At step 206, a ventricular depolarization and a ventricular repolarization are detected in a portion of the first signal corresponding to a cardiac cycle. A QRS complex, such as the one shown in signal 108 of FIG. 1, is indicative of ventricular depolarization. Ventricular depolarization can be detected, e.g., by detected the Q wave of the QRS complex, the R wave of the QRS complex, and/or the S wave of the QRS complex. However, since the R wave is the easiest to detect, due to its relatively large magnitude, it is practical for ventricular depolarization to be detected by detecting the R wave. Accordingly, any known or future developed technique for detecting an R wave (e.g., by peak detection or threshold crossing) can be used to detect ventricular depolarization. Exemplary techniques for detecting R waves are disclosed in U.S. patent application Ser. No. 10/998,026, entitled "Systems and Methods for Detection of VT and VF from Remote Sensing Electrodes" (Nabutovsky et al.), filed Nov. 24, 2004, which is incorporated herein by reference. Alternatively, known or future developed techniques for detecting the Q, R and/or S waves can be used to detect ventricular depolarization.

A T wave, such as the one shown in signal 108 in FIG. 1, is indicative of ventricular repolarization. Accordingly, any known or future developed technique for detecting a T wave can be used to detect ventricular repolarization. Some exemplary techniques for detecting T waves are disclosed in U.S. patent application Ser. No. 10/979,833, entitled "Systems and Methods for Automatically Setting Refractory and Blanking Periods," (Snell and Bharmi) filed Nov. 1, 2004, which is incorporated herein by reference. "Some additional exemplary techniques for detecting T waves are disclosed in U.S. Pat. No. 5,782,887 (van Krieken et al) and U.S. Pat. No. 6,836,682 (Van Dam), which are incorporated herein by reference. Use of alternative techniques for detecting T waves are within are also within the scope of the present invention."

At step 208, a maximum peak amplitude is detected in a portion of the second signal corresponding to the same cardiac cycle referred to in step 206. For the following discussion, it will be assumed that the second signal is a PPG signal. A peak detection circuit, a peak detection algorithm or the like, can be used to detect the peak amplitude of a PPG signal (or other second signal), as is well known in the art. As will be discussed below with reference to step 218, the peak-to-peak amplitude $a_1$ at this point in the second signal (i.e., at the point where the PPG signal amplitude is maximum) should also be determined. Thus, it would be practical to perform steps 208 and 218 at generally the same time.

At step 210, there is a determination of a time $t_1$ from detection of the ventricular depolarization to the detection of the maximum peak amplitude in the second signal. In other words, time $t_1$ is the time from the QRS complex, or a component thereof (e.g., Q wave, R wave or S wave) to the peak of the second signal (e.g., the peak of the PPG signal). An exemplary time $t_1$ is shown in FIG. 1.

Ventricular depolarization occurs at the beginning of systole, which substantially coincides with the end of diastole (ED in FIG. 1). The maximum peak amplitude of the second signal occurs when a mechanical pulse resulting from the ventricular depolarization is detected by the second sensor, which is a distance from a location in the patient's heart where the pulse originated. For example, the second sensor (e.g., a PPG sensor) can be implanted in the pectoral region, e.g., attached directly to (or by a lead to) the housing of a pacemaker, ICD or cardiac monitor, as will be described in more detail below. According, the time $t_1$ is indicative of the time from the beginning of systole (or end of diastole) to the peak in the mechanical pulse detected by an implanted sensor.

At step 212, there is a determination of a time $t_2$ from the detection of the ventricular repolarization to the detection of the maximum peak amplitude in the second signal. As just explained, the maximum peak amplitude of the second signal occurs when a mechanical pulse resulting from the ventricular depolarization is detected by the second sensor, which is a distance from the location in the patient's heart where the pulse originated. As explained above, the T wave in the first signal (i.e., ECG or IEGM) is indicative of ventricular repolarization. Accordingly, the time $t_2$ can be determined by determining the time from the T wave in the first signal (ECG or IEGM) to the time of the peak amplitude in the second signal (e.g., a PPG signal). Ventricular repolarization occurs at the end of systole. Accordingly, the time $t_2$ is indicative of the time from the end of systole to the peak in the mechanical pulse detected by an implanted sensor.

At step 214, a peak pulse arrival time (PPAT) is determined based on times $t_1$ and $t_2$. The diastolic pressure (DP), which is the lowest arterial blood pressure, occurs at the end of diastole (ED in FIG. 1), which substantially coincides with the beginning of systole. The systolic pressure (SP), which is the peak arterial blood pressure, occurs during systole, at a time between the beginning of systole and the end of systole (ES in FIG. 1). In specific embodiments it is assumed that systole is substantially symmetric, and thus that the peak in systole occurs substantially between the beginning and end of systole. Accordingly, in specific embodiments, PPAT is the mean of times $t_1$ and $t_2$. In other words, PPAT can be determined using the equation PPAT=$(t_1+t_2)/2$. In still other embodiments, slight variations on this formula can be used. For example, it may be determined that the value 2 in the denominator of the PPAT equation should be replaced with 1.8 or 2.2, or the like, if it is determined that the peak in systole is slightly asymmetric.

At step 216, a value indicative of systolic pressure (SP) is determined based on the PPAT. PPAT is inversely related to SP, in that the greater the PPAT the lower the SP, and the lower the PPAT the greater the SP. In a simplest embodiment, SP≈1/PPAT. However, it would be preferred to use a patient specific correlation factor (e.g., a constant K) when determining SP. In other words, in specific embodiments, SP=K/PPAT, where K is determined during a calibration procedure. More specifically, an actual value of SP is determined using any known accurate acute technique, and a value of PPAT is measured in the manner described above using an implanted system. This will result in K being the only unknown factor in the equation, and thus, K would be easily calculable (e.g., by an external programmer, or the like). The patient could also be asked to exercise, or could be appropriately paced, to change the patient's SP, to thereby check the accuracy of K over a range of SPs and PPATs. If appropriate, K can be adjusted so that K is accurate over a range of systolic pressures. Presuming PPAT is measured in msec, the units of K can be mmHg msec, so that when K is multiplied by 1/PPAT, the resulting SP has units of mmHg. Use of look up tables and interpolation are also within the scope of the present invention.

In summary, at step 214, SP can be determined based on PPAT using an equation (e.g., SP=K/PPAT), or using a simple look-up table. An alternative equation could be SP=K/PPAT+ $\beta$. In a similar manner as just described, $\beta$ can be determined during a calibration procedure. Other formulas are also possible, and could be derived by determining actual values of the SP for various different values of PPAT, and are within the scope of the present invention.

An exemplary calibration procedure (performed at implant and/or thereafter) will now be explained. During the calibration procedure, actual measures of arterial blood pressure, including SP and DP, are measured along with values of PPAT (and peak-to-peak amplitude $a_1$, as will be discussed below). The actual measure of the patient's SP and DP can be obtained, e.g., using a non-invasive auscultatory or oscillometric techniques, or an invasive intravascular cannula method, or any other acute technique. For a more specific example, actual arterial pressure measurements (SP and DP) can be measured using a high fidelity micronometer-tipped pressure catheter (e.g., model 4F, SPC-340, available from Millar Instruments, Texas), which is placed in the ascending aorta via a carotid arteriotomy. Other techniques are also possible, and within the scope of the present invention.

Still referring to FIG. 2A, at step 218, a peak-to-peak amplitude $a_1$ in the second signal (e.g., a PPG signal) is determined, at the point of the peak amplitude in the second signal (detected at step 208). For example, one or more peak detection circuit can be used to detect the peak-to-peak amplitude $a_1$. Alternatively, software, hardware and/or firmware can be used to detect the peak-to-peak amplitude $a_1$ based on sample data points of the PPG signal, e.g., by determining a difference between maximum and minimum sample values of a PPG signal for each cardiac cycle, or a similar algorithm. An exemplary peak-to-peak amplitude $a_1$ is shown in FIG. 1. As mentioned above, it would be practical to perform steps 208 and 218 at generally the same time.

Steps 220 and 222 will now be discussed together. At step 220, a value indicative of pulse pressure (PP) is determined based on the amplitude $a_1$. At step 222, a value indicative of diastolic pressure (DP) is determined by subtracting the value indicative of PP from the value indicative of SP (i.e., DP=SP−PP). The value indicative of PP is mainly determined so that the value of DP can be determined. Accordingly, steps 220 and 222 together can be collectively thought of as determining a value of DP based on the value of SP (determined at step 216) and the value of $a_1$ (determined at step 218).

Peak-to-peak amplitude $a_1$ is directly related to the PP, in that the greater $a_1$ the greater the PP, and the lower the $a_1$ the lower the PP. In a simplest embodiment, PP≈$a_1$. However, it would be preferred to use a patient specific correlation factor (e.g., a constant M) when determining PP. In other words, in specific embodiments, PP=M·$a_1$, or possibly PP=M·$a_1$+σ, where M (and possibly also σ) can be determined during a calibration procedure, as will be described below.

During calibration, while actual values of SP are being determined for various PPAT values, actual values of DP can also be determined for various values of $a_1$. This will enable the patient specific correlation factor M (and possibly also σ) to be determined during the calibration procedure. For example, by combining PP=M·$a_1$ with DP=SP−PP, a resulting equation is DP=SP−(M·$a_1$). Since actual values of DP and SP can be obtained during calibration (at implant and/or thereafter), and values of $a_1$ can be measured during calibration, the patient specific correlation factor M (and possibly also σ) can be easily determined. Other formulas are also possible, and could be derived by determining actual values of the DP for various different values of $a_1$. After implant, in similar manners as were discussed above with reference to step 218, an algorithm or look-up table can be used to calculate PP based on $a_1$ at step 220.

Once SP and DP are determined (at steps 216 and 222), mean arterial pressure (MAP) can also be determined. For example, the equation MAP=⅓ SP+⅔ DP can be used. Alternatively, the equation MAP=(SP+DP)/2 can be used. Use of other equations is also within the scope of the present invention.

In step 214 described above, the peak pulse arrival time (PPAT) is determined based on times $t_1$ and $t_2$. It is believed that increased accuracy can be obtained by using PPAT in step 216 to determine the systolic pressure (SP), as compared to using a more simple pulse arrival time (PAT). Nevertheless, in alternative embodiments, described with reference to FIG. 2B, at step 214' a pulse arrival time (PAT) is determined based on $t_1$ (but not $t_2$), and at step 216' the systolic pressure (SP) is determined based on PAT. In a simplest embodiment, SP≈1/PAT. Alternatively, SP=K/PAT, or SP=K/PAT+β. In a similar manner as was described above, K (and possibly β) can be determined during a calibration procedure. Other formulas are also possible, and could be derived by determining actual values of the SP for various different values of PAT. Since time $t_2$ is not used to determine PAT, at step 206' ventricular repolarization need not be detected to determine PAT (however, T waves may be detected for other, unrelated reasons). Additionally, step 212 need not be performed, and is thus not shown in FIG. 2B.

In accordance with specific embodiments of the present invention, arterial blood pressure information such as the value indicative of SP (obtained at step 216), the value indicative of DP (obtained at step 222), the value of MAP determined based on SP and DP, and potentially other information is stored within memory of the implantable system for later analysis within the device and/or for later transmission to an external device. Such an external device (e.g., an external programmer or external monitor) can then be used to analyze such data.

Embodiments of the present invention are not limited to the exact order and/or boundaries of the steps shown in FIGS. 2A and 2B. In fact, many of the steps can be performed in a different order than shown, and many steps can be combined, or separated into multiple steps. All such variations are encompassed by the present invention. For example, steps 208 and 218 can be combined into a single step, or step 218 can immediately follow step 208. For another example, step 206 can be separated into two steps, one where ventricular depolarization is detected, and another where ventricular repolarization is detected. The only time order is important is where a step acts on the results of a previous step. For example, PPAT can not be determined at step 216 until times $t_1$ and $t_2$ are determined at steps 212 and 214. However, steps 212 and 214 can be combined, or their order can be swapped.

In accordance with specific embodiments of the present invention, an alarm can be triggered based on comparisons of the values indicative of SP, the values indicative of DP, the changes in SP and/or the changes in DP to corresponding thresholds. Such an alarm can be part of an implanted system. Alternatively, an implanted system can trigger a non-implanted alarm of a non-implanted system. In still other embodiments, where arterial pulse pressure information is transmitted (e.g., via telemetry) to an external device, a non-implanted alarm can be triggered based on comparisons of the values indicative of SP, the values indicative of DP, the changes in SP and/or the changes in DP, received by the non-implanted device, to corresponding thresholds. Values indicative of SP and DP can be used to determine values of indicative of MAP, and corresponding MAP thresholds can be used to trigger alarms or the like.

In accordance with specific embodiments of the present invention, the method described with reference to FIG. 2A or 2B can be repeated from time-to-time, to thereby track changes in SP, DP and/or MAP. For example, steps 202-222 can be performed periodically (e.g., once a minute, hour, day, week, or the like). The values indicative of SP, DP and/or MAP can be compared in real time to corresponding thresholds. Alternatively, or additionally, values indicative of SP, DP and/or MAP can be stored in memory of the implanted system. Such stored values can be analyzed by the implanted system and/or transmitted (e.g., via telemetry) to an external system (e.g., external programmer and external monitor) and analyzed by the external system. Use of various thresholds can be used to trigger alarms and/or therapy, as will be described below.

Depending on the frequency, periodic monitoring of arterial blood pressure may be costly in terms of energy, memory and/or processing resources. Accordingly, it may be more efficient to trigger the performance of certain steps upon detection of an event, such as a specific activity, or lack thereof, and/or a specific posture of the patient. For example, an activity sensor and/or posture sensor can be used to trigger the performance of steps 202-222. For example, steps 202-222 can be triggered when it is detected that a patient is inactive and lying down. Additionally, or alternatively, steps 202-222 can be triggered when a patient is upright and walking. In still other embodiments, steps 202-222 can be triggered to occur, at specific intervals following a patient changing their posture (e.g., assuming an upright posture) and/or activity level. For example, following a triggering event, values of arterial blood pressure can be determined once a minute for 10 minutes, or at 1 minute, 2 minutes, 5 minutes and 10 minutes after the triggering event. Of course, other variations are also possible, and within the scope of the present invention. It may also be that one or more specific step, such as step 202, is performed substantially continually (e.g., because the signals obtained at step 202 are also used for pacing, arrhythmia detection, and the like), but other steps (e.g., steps 204-222) are only performed in response to a triggering event, such as those discussed above.

To detect posture and/or activity, an implantable system can include a sensor, which can detect a patient's posture and/or level of activity. The sensor can be, e.g., a DC-coupled 3-dimensional accelerometer as described in U.S. Pat. No. 6,658,292 (Kroll et al), a multi-axis DC accelerometer as described in U.S. Pat. No. 6,466,821 (Pianca et al), or an external field sensor as described in U.S. Pat. No. 6,625,493 (Kroll et al), each of which are incorporated herein by reference. Such sensors are able to distinguish among different static positions. In addition, since the sensors can detect motion, they can be used to distinguish between a static vertical position, such as sitting, and a standing position, which due to the dynamics of balance is associated with subtle motion that is not present while sitting. In this way an implantable system, using one of the above mentioned sensors or other sensing modality, can detect a change in body position (i.e., posture), which can be used as a trigger to perform specific methods of the present invention described below.

It is normal for there to be a normal circadian variation in arterial blood pressure values, including SP, DP and MAP values. For example, a drop in such values when a patient is sleeping, at rest and/or supine is normal. However, a drop in such values when a patient is active, or upright, or within a short period of a patient assuming an upright posture, is abnormal. Implanted activity and/or posture sensors can thus be used to assist in defining when an alarm or the like should be triggered. For example, a posture sensor can be used to trigger the monitoring of arterial blood pressure values when a patient assumes an upright posture. In this manner, such monitoring can be used to determine whether a drop in blood pressure within a specific amount of time (e.g., 10 minutes), following the patient assuming of an upright position, exceeds a specified threshold. Such a threshold can be, e.g., an absolute value or a percentage. In specific embodiments, the SP, DP and/or MAP thresholds to which determined SP, DP and/or MAP values are compared can be based on the activity and/or posture of the patient.

Where at least some of steps 202-222 are triggered in response to detection of various different activity and/or posture states, information about the patient's activity and/or posture can also be stored along with the arterial blood pressure information, so that such information can be correlated. In other words, there could be a cross-correlation of arterial blood pressure values with levels of activity and/or posture.

Additionally, or alternatively, the implantable system can also monitor for episodes and degrees of myocardial ischemia, and there could be a cross-correlation of arterial blood pressure values with degrees of ischemia (as well as with levels of activity and/or posture). This can be useful, e.g., for determining the seriousness associated with ischemic episodes. For example, severe ischemia associated with a drop in arterial blood pressure at low levels of activity is more serious than a mild degree of ischemia with no drop in blood pressure at high levels of activity.

In specific embodiments, the implanted system can detect myocardial ischemic events based on the ECG/IEGM signals obtained at step 202. For example, known techniques can be used that perform ST-segment shift analysis to determine if there is a deviation of the ST-segment from a baseline (e.g., a PQ segment baseline), and detect myocardial ischemic events when the deviation is beyond a threshold. Other techniques are also possible. The precise technique used to detect episodes of myocardial ischemia are not important to the present invention. Rather, what is important is that episodes of myocardial ischemia can be detected, so that such information can be correlated with arterial blood pressure information, and preferably information showing such correlations can be stored. For example, the implantable system can store, in memory, arterial blood pressure data (obtained using embodiments of the present invention) corresponding to the period immediately prior to, during and subsequent to a detected myocardial ischemic episode. The implantable device can also store data that identifies the ST-segment level during various portions of an episode (e.g., at onset of the ischemia, the peak of the ischemia and the termination of the ischemia), the time of the ischemic episodes (at onset, at peak and/or at termination), the duration of the episode, as well as any other type of information that a physician may deem useful. U.S. Pat. Nos. 6,112,116, 6,272,379 and 6,609,023 (all to Fischell et al.), which are incorporated herein by reference, provide exemplary additional details of the types of data that can be stored in response to the detection of a myocardial ischemic episode, and how such data can be efficiently and effectively stored. Additionally, corresponding arterial blood pressure information, such as values indicative of SP, DP and/or MAP can also be stored. This would enable the implantable system, or an external system and/or physician (which receives the information from the implantable system) to analyze how such conditions are inter-related.

Accordingly, embodiments of the present invention can be used to determine, or assist with the determination of, whether there is a correlation between levels of arterial blood pressure, levels of activity and/or posture, and myocardial ischemic episodes experienced by a patient. Such information will enable a medical practitioner to analyze whether ischemic episodes that the patient experienced may have precipitated changes in arterial blood pressure, posture and/or activity.

In accordance with specific embodiments of the present invention, measures of arterial blood pressure, including values indicative of SP, DP and/or MAP, can be used for pacing interval optimization, as well as pacing rate optimization. Exemplary pacing intervals include, but are not limited to, atrio-ventricular (RA-RV) delay, interventricular (RV-LV) delay, interatrial (RA-LA) delay and intraventricular (RV1-RV2 or LV1-LV2) delay. This can include adjusting the pacing interval(s) to attempt to maintain the patient's arterial blood pressure at a specified level(s). The specified level(s) can be an optimal level(s), e.g., as specified by a physician. In specific embodiments, this can include increasing or decreasing specific pacing intervals, or combinations thereof, to attempt to increase or decrease values indicative of arterial blood pressure. In other words, measures of arterial blood pressure, determined in accordance with embodiments of the present invention, can be used for closed loop adjustments of pacing parameters.

More generally, measures of arterial blood pressure, obtained in accordance with embodiments of the present invention can be used to assess the hemodynamic status of a patient. This can include tracking a patient's cardiac disease state, including but not limited to, heart failure. For example, increases in measures of arterial blood pressure over time can be interpreted as a worsening of a heart failure condition.

Measures of arterial blood pressure, obtained using embodiments of the present invention, can be used for arrhythmia discrimination, including tachyarrhythmia classification. For example, it is believed that before the onset of a tachyarrhythmia, there will be a detectable drop in arterial blood pressure (e.g., DP, SP and/or MAP). If the patient is experiencing an atrial tachyarrhythmia, it is believed that the arterial blood pressure will return to normal levels as the tachyarrhythmia progresses. In contrast, if the patient is experiencing a ventricular tachyarrhythmia, it is believed that the arterial blood pressure will remain low during the ventricular tachyarrhythmia. Accordingly, measures of arterial blood pressure can be used to distinguish atrial tachyarrhythmias from ventricular tachyarrhythmias. If there are instances where the arterial blood pressure staying low makes it difficult to determine PPAT, determinations of PAT may be used in place of PPAT, in accordance with specific embodiments of the present invention.

Measures of arterial blood pressure can also be used to classify a tachyarrhythmia as either hemodynamically stable or unstable. For example, where arterial blood pressure generally stays within an acceptable range during a tachyarrhythmia, the tachyarrhythmia can be considered hemodynamically stable. In contrast, where arterial blood pressure significantly drops (or increases) due to the tachyarrhythmia, the tachyarrhythmia can be considered hemodynamically unstable. Such determinations of hemodynamic stability can be used to enable, adjust and/or abort certain stimulation therapies, including anti-tachycardia pacing (ATP) and/or shock therapy.

In the past, measures of arterial blood pressure have not generally been available before, at the onset, and during the progression of spontaneous tachyarrhythmias. By monitoring arterial blood pressure, using embodiments of the present invention, additional information about the relationships between arterial blood pressure and tachyarrhythmias can be obtained. Such information can be very useful for detecting the onset of tachyarrhythmias, for possibly determining the cause of specific tachyarrhythmias, and for selecting, adjusting and/or aborting specific types of therapy.

Figure 3A:
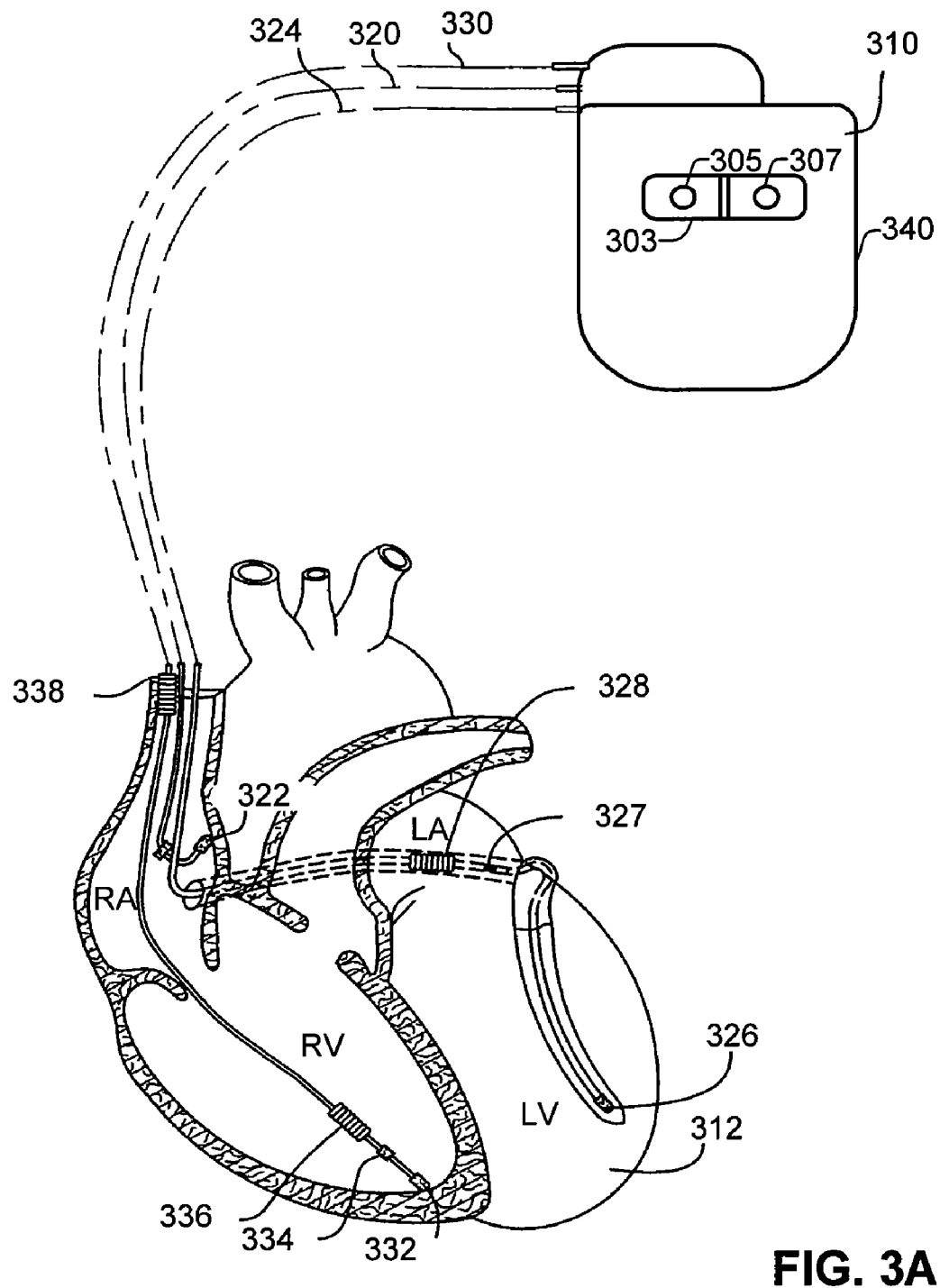
FIG. 3A illustrates an exemplary implantable stimulation device that includes a PPG sensor, and which can be used to perform embodiments of the present invention.
Figure 3B:
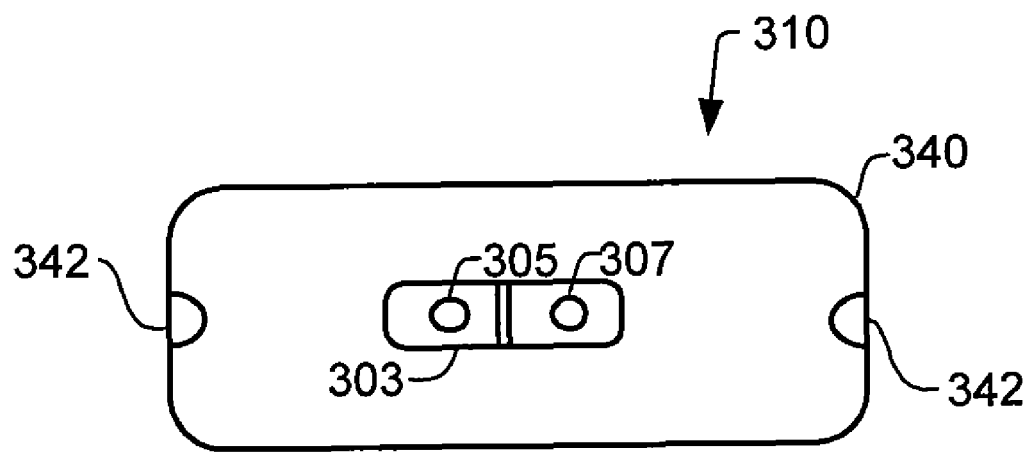
FIGS. 3B and 3C illustrates exemplary implantable monitoring devices that include a PPG sensor, and which can be used to perform embodiments of the present invention.

FIGS. 3A and 3B will now be used to describe an exemplary implantable system that can be used to determine values indicative of arterial blood pressure, in accordance with embodiments of the present invention. Referring to FIG. 3A, the implantable system is shown as including an implantable stimulation device 310, which can be a pacing device and/or an implantable cardioverter defibrillator. The device 310 is shown as being in electrical communication with a patient's heart 312 by way of three leads, 320, 324 and 330, which can be suitable for delivering multi-chamber stimulation and shock therapy. The leads can also be used to obtain IEGM signals, for use in embodiments of the present invention. In instead of having leads with electrodes attached to the heart, it is also possible that subcutaneous electrodes can be used to obtain ECG signals. In still other embodiments, it's possible that the electrodes are located on the housing of the implantable device 310, and that such electrodes are used to obtain subcutaneous ECG signals. In this latter embodiment, the device 310 may not be capable of pacing and/or defibrillation, but rather, the implantable device 310 can be primarily for monitoring purposes.

The implantable system is also shown as including an implantable photoplethysmography (PPG) sensor 303 that can be used to produce a PPG signal, similar to signal 108 shown in FIG. 1. Referring to FIG. 3A, the PPG 303 sensor includes a light source 305 and a light detector 307. The light source 305 can include, e.g., at least one light-emitting diode (LED), incandescent lamp or laser diode. The light detector 307 can include, e.g., at least one photoresistor, photodiode, phototransistor, photodarlington or avalanche photodiode. Light detectors are often also referred to as photodetectors or photocells.

The light source 305 outputs light that is reflected or backscattered by surrounding patient tissue, and reflected/backscattered light is received by the light detector 307. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. Additional details of exemplary implantable PPG sensors are disclosed in U.S. Pat. Nos. 6,409,675 and 6,491,639, both entitled "Extravascular Hemodynamic Sensor" (both Turcoft), which are incorporated herein by reference.

A PPG sensor can use a single wavelength of light, or a broad spectrum of many wavelengths. In the alternate embodiments, the light source can be any source of radiant energy, including laserdiode, heated filament, and ultrasound transducer. The detector can be any detector of radiant energy, including phototransistor, photodetector, ultrasound transducer, piezoelectric material, and thermoelectric material.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 302 can be attached to a housing 340 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004, which is incorporated herein by reference. It is also possible that the PPG sensor 302 be integrally part of the implantable cardiac stimulation device 310. For example, the PPG sensor 302 can be located within the housing 340 of an ICD (or pacemaker) that has a window through which light can be transmitted and detected. In a specific embodiment, the PPG sensor 302 has a titanium frame with a light transparent quartz window that can be welded into a corresponding slot cut in the housing of the ICD. This will insure that the ICD enclosure with the welded PPG sensor will maintain a hermetic condition.

Where the PPG sensor is incorporated into or attached to a chronically implantable device 310, the light source 305 and the light detector 307 can be mounted adjacent to one another on the housing or header of the implantable device. The light source 305 and the light detector 307 are preferably placed on the side of the implantable device 310 that, following implantation, faces the chest wall, and are configured such that light cannot pass directly from the source to the detector. The placement on the side of the device 310 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 305 and the light detector 307 can be placed on the face of the device 310 that faces the skin of the patient.

The implantable PPG sensor 303 outputs a PPG signal similar to signal 108 shown in FIG. 1. More specifically, the output of the light detector 305 can be an analog signal that resembles signal 108. Such a signal can be filtered and/or amplified as appropriate, e.g., to remove respiratory affects on the signal, and the like. Additionally, the signal can be digitized using an analog to digital converter. Based on the PPG signal, and an ECG or IEGM obtained using implanted electrodes, times $t_1$, $t_2$ and peak-to-peak amplitude $a_1$, which were discussed above with reference to FIGS. 1, 2A and 2B, can be determined, thereby enabling measures of SP, DP and MAP to be determined in accordance with embodiments of the present invention.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals.

In specific embodiments, the arterial plethysmography signal can be produced using non-radiant methods and devices, including, but not limited to mechanical strain, electrical impedance, or pressure. More specifically, rather than using a PPG sensor that includes a light source and detector, the implanted plethysmography sensor can include a strain gauge, a linear displacement sensor, or an ultrasound transducer, each of which is known in the art. Alternatively, an impedance plethysmography sensor, which is also known in the art, can be used. Details of exemplary implantable sensors that produce an impedance plethysmography signals are disclosed, e.g., in U.S. Pat. Nos. 4,674,518, 4,686,987 and 5,334,222 (all to Salo), which are incorporated herein by reference.

Still referring to FIG. 3A, to sense atrial cardiac signals and to provide right atrial chamber stimulation therapy, the device 310 is coupled to an implantable right atrial lead 320 having at least an atrial tip electrode 322, which typically is implanted in the patient's right atrial appendage. To sense left atrial and ventricular cardiac signals and to provide left-chamber pacing therapy, the device 310 is coupled to a "coronary sinus" lead 324 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

The device 310 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode 336 will be positioned in the right ventricle and the SVC coil electrode 338 will be positioned in the superior vena cava. Accordingly, the right ventricular lead 330 is capable of receiving cardiac signals and delivering stimulation in the form of pacing and shock therapy to the right ventricle.

Figure 3C:
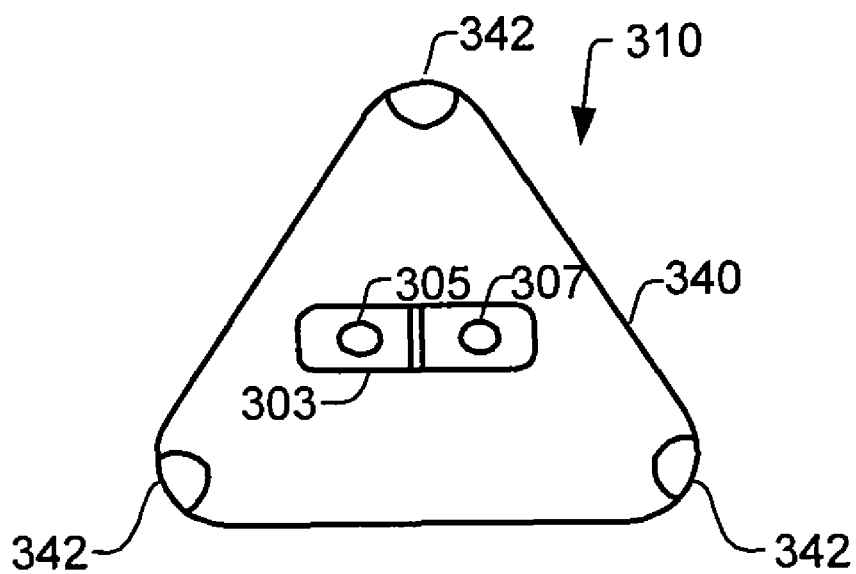

FIG. 3B illustrates an alternative embodiment of the implantable device 310. Here a housing 340 of the device is shown as small, thin, and oblong, with smooth surfaces and a physiologic contour which minimizes tissue trauma and inflammation. The oblong geometry of the housing 340 is desirable because it maximizes separation of electrodes 342 and prevents rotation of the monitor within the tissue pocket, thereby allowing interpretation of morphology features in an ECG sensed using electrodes 342. Two ECG electrodes 432 are shown, however more can be present. In the alternate embodiment illustrated in FIG. 3C, three ECG electrodes 342 are present, one at each apex of the triangle formed by the device housing 340. These three electrodes allow the three standard surface ECG leads I-III to be approximated. In another embodiment, four or more ECG electrodes might be used, with each orthogonal electrode pair providing orthogonal ECG signals. Alternatively, an embodiment lacking ECG electrodes is possible. A further alternative has a single ECG electrode with the monitor housing acting as the other electrode in the pair. U.S. Pat. No. 6,409,675, which was incorporated above by reference, in its discussion of FIGS. 2a-2c and 3a-3c provides some additional details of an implantable monitor that includes ECG electrodes on its housing and a PPG sensor. FIGS. 3B and 3C show that the implantable device 310 also include a PPG sensor 303. However, the implantable device 310 can additionally or alternatively include another implantable sensor that obtains an alternative type of plethysmography signal, examples of which were discussed above.

Figure 4:
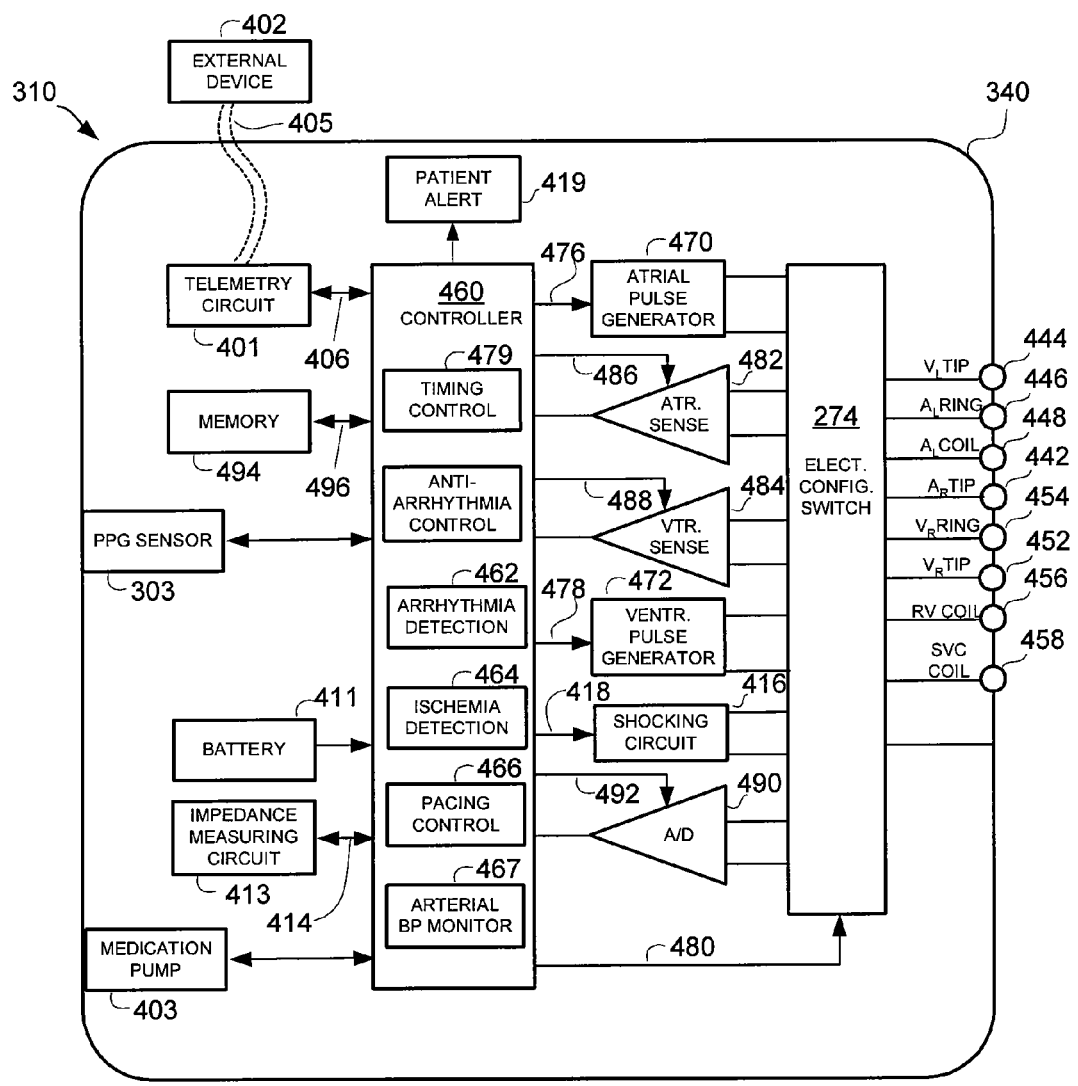
FIG. 4 is a simplified block diagram that illustrates possible components of the implantable devices shown in FIGS. 3A-3C.

FIG. 4 will now be used to provide some exemplary details of the components of the implantable devices 310. Referring now to FIG. 4, each of the above implantable devices 310, and alternative versions thereof, can include a microcontroller 460. As is well known in the art, the microcontroller 460 typically includes a microprocessor, or equivalent control circuitry, and can further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing and data analysis functions are well known in the art. In specific embodiments of the present invention, the microcontroller 460 performs some or all of the steps associated with determining values of arterial blood pressure, detecting episodes of myocardial ischemia, and performing pacing interval optimization. Additionally, the microcontroller 460 may detect arrhythmias, and select and control delivery of anti-arrhythmia therapy.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 310 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, where the implantable device is a monitor that does not provide any therapy, it is clear that many of the blocks shown may be eliminated.

The housing 340, shown schematically in FIG. 4, is often referred to as the "can", "case" or "case electrode" and may be programmably selected to act as the return electrode for all "unipolar" modes. The housing 340 may further be used as a return electrode alone or in combination with one or more of the coil electrodes, 128, 136 and 138, for shocking purposes. The housing 340 can further include a connector (not shown) having a plurality of terminals, 442, 444, 446, 448, 452, 454, 456, and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 322.

To achieve left atrial and ventricular sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 148, which are adapted for connection to the left ventricular ring electrode 326, the left atrial tip electrode 327, and the left atrial coil electrode 328, respectively.

To support right ventricle sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 332, right ventricular ring electrode 334, the RV coil electrode 136, and the SVC coil electrode 138, respectively.

An atrial pulse generator 470 and a ventricular pulse generator 472 generate pacing stimulation pulses for delivery by the right atrial lead 320, the right ventricular lead 330, and/or the coronary sinus lead 324 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuits 482 and ventricular sensing circuits 484 may also be selectively coupled to the right atrial lead 320, coronary sinus lead 324, and the right ventricular lead 330, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables the device 310 to deal effectively with the difficult problem of sensing the low amplitude signal characteristics of atrial or ventricular fibrillation. Such sensing circuits, 482 and 484, can be used to determine cardiac performance values used in the present invention. Alternatively, an automatic sensitivity control circuit may be used to effectively deal with signals of varying amplitude.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 310 includes an arrhythmia detector 462 that utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation) can be classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 462 can perform arrhythmia discrimination, e.g., using measures of arterial blood pressure determined in accordance with embodiments of the present invention. Exemplary details of such arrhythmia discrimination, including tachyarrhythmia classification, are discussed above. The arrhythmia detector 462 can be implemented within the microcontroller 460, as shown in FIG. 4. Thus, this detector 462 can be implemented by software, firmware, or combinations thereof. It is also possible that all, or portions, of the arrhythmia detector 462 can be implemented using hardware. Further, it is also possible that all, or portions, of the ischemia detector 462 can be implemented separate from the microcontroller 460.

Two exemplary types of arrhythmias that the arrhythmia detector 462 can detect include ventricular tachycardia (VT) and ventricular fibrillation (VF). A tachycardia is a fast heart rate (usually over 100 beats per minute) typically caused by disease or injury. It can also be part of a normal response to increased activity or oxygen demands. The average heart beats between 60 and 100 times per minute. When the tachycardia is due to disease or injury, it usually requires treatment. Tachycardias may begin in the upper chambers of the heart (the atria) or the lower chambers of the heart (the ventricles). A ventricular tachycardia (VT) begins in the ventricles. Some are harmless, but others are life threatening in that they can quickly deteriorate to a ventricular fibrillation.

A ventricular fibrillation (VF) is a very fast, chaotic heart rate (usually over 102 beats per minute) in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF quickly becomes more erratic, resulting in sudden cardiac arrest. This arrhythmia must be corrected immediately via a shock from an external defibrillator or an implantable cardioverter defibrillator (ICD). The defibrillator stops the chaotic electrical activity and restores normal heart rhythm.

These are just two examples of the types of arrhythmias that the arrhythmia detector 462 can detect. One of ordinary skill in the art will appreciate that other types of arrhythmias can be detected, and information for such other types of arrhythmias can be stored. Examples of other types of arrhythmias that can be detected by the detector 462 include, but are not limited to, supraventricular arrhythmias (SVAs), such as supraventricular tachycardias (SVTs), atrial flutter (AF) and/or atrial fibrillation (AF)

In accordance with embodiments of the present invention, the implantable device 310 includes an arterial blood pressure monitor 467, which can determine values indicative of SP, DP and/or MP, using the techniques described above with reference to FIGS. 1, 2A and 2B. The arterial blood pressure monitor 467 can be implemented within the microcontroller 460, as shown in FIG. 4, and can the be implemented by software, firmware, or combinations thereof. It is also possible that all, or portions, of the monitor 467 to be implemented using hardware. Further, it is also possible that all, or portions, of the monitor 467 to be implemented separate from the microcontroller 460. The arterial blood pressure monitor 467 can be used in a closed loop control system to provide an assessment of hemodynamic stability during pacing parameter adjustments, and/or as an assessment of hemodynamic stability during a detected arrhythmia. Such measures of hemodynamic stability can be used when determining which anti-arrhythmia therapy options are appropriate.

In accordance with embodiments of the present invention, the implantable device 310 also includes an ischemia detector 464, which can detect ischemic events based, e.g., on ST-segment shift analysis. The ischemia detector 464 can be implemented within the microcontroller 460, as shown in FIG. 4. Thus, this detector 464 can be implemented by software, firmware, or combinations thereof. It is also possible that all, or portions, of the ischemia detector 464 can be implemented using hardware. Further, it is also possible that all, or portions, of the ischemia detector 464 can be implemented separate from the microcontroller 460.

The ischemia detector 464 can monitor sensed cardiac signals in order to detect and record timing and duration information relating to myocardial ischemic episodes. Ischemia detector 464 may also trigger a patient or physician alert in response to detecting a myocardial ischemic event. For example, a patient alert 419, which produces a vibratory or auditory alert, may be triggered.

There are many documented techniques for detecting episodes of myocardial ischemia. Many of these techniques perform ST-segment shift analysis to determine if there is a deviation of the ST-segment from a baseline (e.g., a PQ segment baseline), and detect myocardial ischemic events when the deviation is beyond a threshold. Other techniques are also possible. The precise technique used by the ischemia detector 464 to detect episodes of myocardial ischemia are not important to the present invention. Rather, what is important is that the ischemia detector 464 can detect episodes of myocardial ischemia and cause information relating to these episodes to be stored. For example, the implantable device 310 can store, in memory 494, IEGM data and/or arterial blood pressure data corresponding to the period immediately prior to, during and subsequent to a detected myocardial ischemic episode. The implantable device can also store data that identifies the ST-segment level during various portions of an episode (e.g., at onset of the ischemia, the peak of the ischemia and the termination of the ischemia), the time of the ischemic episodes (at onset, at peak and/or at termination), the duration of the episode, as well as any other type of information that a physician may deem useful. U.S. Pat. Nos. 6,112,116, 6,272, 379 and 6,609,023 (all to Fischell et al.), which are incorporated herein by reference, provide exemplary additional details of the types of data that can be stored in response to the detection of a myocardial ischemic episode, and how such data can be efficiently and effectively stored.

The implantable device 310 can also include a pacing controller 466, which can adjust a pacing rate and/or pacing intervals based on measures of arterial blood pressure, in accordance with embodiments of the present invention. The pacing controller 466 can be implemented within the microcontroller 460, as shown in FIG. 4. Thus, the pacing controller 466 can be implemented by software, firmware, or combinations thereof. It is also possible that all, or portions, of the pacing controller 466 can be implemented using hardware.

Further, it is also possible that all, or portions, of the pacing controller 466 can be implemented separate from the microcontroller 460.

The implantable device can also include a medication pump 403, which can deliver medication to a patient if the patient's arterial blood pressure levels exceed or fall below specific thresholds. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 4, cardiac signals are also applied to the inputs of an analog-to-digital (A/D) data acquisition system 490. The data acquisition system 490 is configured to acquire IEGM and/or ECG signals, convert the raw analog data into a digital signal, and store the digital signals for later processing and/or telemetric transmission to an external device 402. The data acquisition system 490 can be coupled to the right atrial lead 320, the coronary sinus lead 324, and the right ventricular lead 330 through the switch 474 to sample cardiac signals across any pair of desired electrodes. In specific embodiments, the data acquisition system 490 may be used to acquire IEGM signals for the analysis of changes in the ST-segment for detecting myocardial ischemia, and for monitoring arterial blood pressure using techniques described above.

The data acquisition system 490 can be coupled to the microcontroller 460, or other detection circuitry, for detecting an evoked response from the heart 312 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 460 is further coupled to the memory 494 by a suitable data/address bus 496, wherein the programmable operating parameters used by the microcontroller 460 are stored and modified, as required, in order to customize the operation of the implantable device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy. The memory 494 can also store arterial blood pressure data.

The operating parameters of the implantable device 310 may be non-invasively programmed into the memory 494 through a telemetry circuit 401 in telemetric communication with an external device 402, such as a programmer, transtelephonic transceiver, or a diagnostic system analyzer. The telemetry circuit 401 can be activated by the microcontroller 460 by a control signal 406. The telemetry circuit 401 advantageously allows intracardiac electrograms and status information relating to the operation of the device 310 (as contained in the microcontroller 460 or memory 494) to be sent to the external device 402 through an established communication link 404. The telemetry circuit can also be use to transmit arterial blood pressure data to the external device 402.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 310 additionally includes a battery 411 which provides operating power to all of the circuits shown in FIG. 4. If the implantable device 310 also employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected.

The implantable device 310 can also include a magnet detection circuitry (not shown), coupled to the microcontroller 460. It is the purpose of the magnet detection circuitry to detect when a magnet is placed over the implantable device 310, which magnet may be used by a clinician to perform various test functions of the implantable device 310 and/or to signal the microcontroller 460 that the external programmer 402 is in place to receive or transmit data to the microcontroller 460 through the telemetry circuits 401.

As further shown in FIG. 4, the device 310 is also shown as having an impedance measuring circuit 413 which is enabled by the microcontroller 460 via a control signal 414. The known uses for an impedance measuring circuit 413 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 413 is advantageously coupled to the switch 474 so that any desired electrode may be used. The impedance measuring circuit 413 is not critical to the present invention and is shown only for completeness.

In the case where the implantable device 310 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (11 to 40 Joules), as controlled by the microcontroller 460. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 340 may act as an active electrode in combination with the RV electrode 336, or as part of a split electrical vector using the SVC coil electrode 338 or the left atrial coil electrode 328 (i.e., using the RV electrode as a common electrode).

The above described implantable device 310 was described as an exemplary pacing device. One or ordinary skill in the art would understand that embodiments of the present invention can be used with alternative types of implantable devices. Accordingly, embodiments of the present invention should not be limited to use only with the above described device.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 2A and 2B. Further, it is possible to change the order of some of the steps shown in FIGS. 2A and 2B, without substantially changing the overall events and results. For another example, it is possible to change the boundaries of some of the blocks shown in FIG. 4.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for monitoring a patient's arterial blood pressure with an arterial blood pressure monitor, the method comprising:
   (a) using implanted electrodes to obtain a first signal indicative of electrical activity of the patient's heart;
   (b) using an implanted sensor to obtain a second signal indicative of mechanical activity of the patient's heart;
   (c) transmitting said first and said second signal to said arterial blood pressure monitor, said arterial blood pressure monitor comprising a microcontroller;
   (d) detecting with said microcontroller a ventricular depolarization and a ventricular repolarization in a portion of the first signal corresponding to a cardiac cycle;
   (e) detecting with said microcontroller a maximum peak amplitude in a portion of the second signal corresponding to the same cardiac cycle;
   (f) determining with said microcontroller a time $t_1$ from the detected ventricular depolarization to the detected maximum peak amplitude in the second signal;
   (g) determining with said microcontroller a time $t_2$ from the detected ventricular repolarization to the detected maximum peak amplitude in the second signal;
   (h) determining with said microcontroller a peak pulse arrival time (PPAT) based on times $t_1$ and $t_2$; and
   (i) determining with said microcontroller a value indicative of systolic pressure (SP) based on the PPAT.

2. The method of claim 1, wherein:
   step (h) comprises determining PPAT by determining a mean of times $t_1$ and $t_2$ with said microcontroller.

3. The method of claim 1, further comprising calibrating the implantable system by:

(i) obtaining accurate measures of the patient's systolic (SP) pressure using a non-implanted device and/or an acutely implanted device;
   (ii) using the implanted electrodes and the implanted sensor to determine a peak pulse arrival time (PPAT) corresponding each of a plurality of accurate measures of the patient's SP; and
   (iii) using the accurate measures of SP and the corresponding PPATs to determine one or more patient specific correlation factor that enables values indicative of the patient's SR to be calculated based on PPAT with said microcontroller; and
   wherein step (i) includes using the one or more patient specific correlation factor when determining the value indicative of SP with said microcontroller.

4. The method of claim 1, further comprising:
   (j) determining a peak-to-peak amplitude $a_1$ in the second signal with said microcontroller; and
   (k) determining a value indicative of diastolic pressure (DP) based on the amplitude al and the value indicative of SP with said microcontroller.

5. The method of claim 4, wherein step (k) includes:
   (k 1) determining a value indicative of pulse pressure (PP) based on the amplitude $a_1$ with said microcontroller;
   (k 2) determining the value indicative of DP by subtracting the value indicative of PP from the value indicative of SP.

6. The method of claim 4, further comprising calibrating the implantable system by:
   (i) obtaining accurate measures of the patient's systolic pressure (SP) and diastolic pressure (DP) using a non-implanted device and/or an acutely implanted device;
   (ii) using the implanted electrodes and the implanted sensor with said microcontroller to determine a peak pulse arrival time (PPAT) and a peak-to-peak amplitude $a_1$ corresponding each of a plurality of accurate measures of the patient's SP and DP; and
   (iii) using the accurate measures of SP and DP and the corresponding PPATs and peak-to-peak amplitudes $a_1$ with said microcontroller to determine patient specific correlation factors that enable values indicative of the patient's SP and values indicative of the patient's DP to be to be calculated based on PPAT and $a_1$, and
   wherein step (i) includes using at least one of the patient specific correlation factors when determining the value indicative of SP; and
   wherein step (k) includes using at least one of the patient specific correlation factors when determining the value indicative of DP.

7. The method of claim 4, further comprising:
   repeating steps (a) through (k) over time to thereby track changes in SP and DP.

8. The method of claim 7, further comprising using an activity sensor and/or posture sensor to trigger the performance of at least some of steps (a) through (k).

9. The method of claim 7, further comprising:
   triggering an alarm with said microcontroller based on comparisons of the values indicative of SP, the values indicative of DP, the changes in SP and/or the changes in DP to corresponding thresholds.

10. The method of claim 7, wherein:
    the arterial blood pressure monitor further comprises a memory and a telemetry circuit;
    step (i) includes storing the value indicative of SP in said memory;
    step (k) includes storing the value indicative of DP in said memory;

and further comprising wirelessly transmitting data indicative of the stored values indicative of SP and DP to a non-implanted device with said telemetry circuit.

11. The method of claim 10, further comprising:
triggering a non-implanted alarm based on comparisons of the values indicative of SP, the values indicative of DP, the changes in SP and/or the changes in DP, received by the non-implanted device, to corresponding thresholds.

12. The method of claim 7, further comprising:
using the values indicative of SP and/or DP for pacing parameter adjustment with said microcontroller or a non-implanted device.

13. The method of claim 7, further comprising:
monitoring for episodes of myocardial ischemia with said microcontroller; and
correlating detected episodes of myocardial ischemia with values indicative of SP and/or DP with said microcontroller.

14. The method of claim 1, wherein the first signal comprises:
an intracardiac electrogram (IEGM) obtained using one or more electrode of an endocardial lead;
or an electrocardiogram (ECG) obtained using one or more subcutaneous or other ECG electrode.

15. The method of claim 1, wherein the second signal comprises a plethysmography signal.

16. The method of claim 15, wherein the plethysmography signal comprises a photoplethysmography signal obtained using an implanted extravascular photoplethysmography sensor.

17. The method of claim 15, wherein the plethysmography signal comprises an impedance plethysmography signal obtained using an implanted impedance sensor.

18. The method of claim 1, wherein the second signal comprises a signal obtained using an implanted sensor including a piezo-electric diaphragm.

19. The method of claim 1, wherein step (d) includes:
detecting the ventricular depolarization by detecting with said microcontroller an R-wave in the portion of the first signal corresponding to the cardiac cycle; and
detecting the ventricular repolarization by detecting with said microcontroller a T-wave in the portion of the first signal corresponding to the cardiac cycle.

20. The method of claim 1, wherein at least some of the steps are performed with the microcontroller in response to a triggering event detected using an implanted sensor that detects posture and/or activity.

21. An implantable system configured to monitor a patient's arterial blood pressure, comprising:
a first detector configured to detect ventricular depolarizations and ventricular repolarizations in cardiac cycles represented in a first signal that is indicative of electrical activity of a patient's heart, wherein the first signal comprises an intracardiac electrogram (IEGM) or an electrocardiogram (ECG);
a sensing circuit to obtain the first signal using implantable electrodes;
a second detector configured to detect maximum peak amplitudes in cardiac cycles represented in a second signal indicative of mechanical activity of the patients' heart;
an arterial blood pressure monitor configured to determine a time $t_1$ from a detected ventricular depolarization to a detected maximum peak amplitude in the second signal;
determine a time $t_2$ from the detected ventricular repolarization to the detected maximum peak amplitude in the second signal;
determine a peak pulse arrival time (PPAT) based on times $t_1$ and $t_2$; and determine a value indicative of systolic pressure (SP) based on the PPAT.

22. The implantable system of claim 21, wherein:
the second signal comprises a plethysmography signal.

23. The implantable system of claim 22, further comprising:
an implantable plethysmography sensor to obtain the second signal.

24. The implantable system of claim 23, wherein the implantable plethysmography sensor comprises a photoplethymography sensor.

25. The implantable system of claim 21, wherein the arterial blood pressure monitor is also configured to:
determine a value indicative of pulse pressure (PP) based on the amplitude $a_1$; and
determine a value indicative of diastolic pressure (DP) by subtracting the value indicative of PP from the value indicative of SP.

26. The implantable system of claim 25, wherein the arterial blood pressure monitor can track changes in SP and DP over time.

* * * * *